US010695013B2

(12) United States Patent
Popp et al.

(10) Patent No.: US 10,695,013 B2
(45) Date of Patent: Jun. 30, 2020

(54) FILTER DEVICE FOR A COLLIMATOR OF AN IRRADIATION DEVICE

(71) Applicant: Siemens Healthcare GmbH, Erlangen (DE)

(72) Inventors: Stefan Popp, Wiesenttal (DE); Robert Petrik, Waldsassen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/263,046

(22) Filed: Jan. 31, 2019

(65) Prior Publication Data
US 2019/0239829 A1 Aug. 8, 2019

(30) Foreign Application Priority Data
Feb. 8, 2018 (DE) .................. 10 2018 201 976

(51) Int. Cl.
*A61B 6/06* (2006.01)
*G21K 1/02* (2006.01)
*G21K 1/04* (2006.01)

(52) U.S. Cl.
CPC ............... *A61B 6/06* (2013.01); *G21K 1/025* (2013.01); *G21K 1/046* (2013.01)

(58) Field of Classification Search
CPC . A61B 6/06; G21K 1/025; G21K 1/04; G21K 1/043; G21K 1/046
See application file for complete search history.

(56) References Cited

U.S. PATENT DOCUMENTS

| 4,909,600 A * | 3/1990 | Ciarlei ................. G02B 26/008 250/233 |
| 2010/0157247 A1 | 6/2010 | Grover et al. |
| 2010/0189216 A1 | 7/2010 | Yuan |

FOREIGN PATENT DOCUMENTS

EP        2210561 A1    7/2010

OTHER PUBLICATIONS

German Patent Document dated Sep. 20, 2018 for German Application No. 102018201976.2.

* cited by examiner

*Primary Examiner* — Chih-Cheng Kao
(74) *Attorney, Agent, or Firm* — Harness, Dickey & Pierce, P.L.C.

(57) ABSTRACT

A filter device is for a collimator of an irradiation device. In an embodiment, the filter device includes a plurality of filter disks, arranged on a disk that is rotatable around an axis. Each filter disk is mounted so as to be movable in a radial direction and is tensioned by way of a respective spring element radially away from the axis or toward the axis against a guide contour, effecting a radial movement of at least one filter disk.

20 Claims, 4 Drawing Sheets

FILTER DEVICE FOR A COLLIMATOR OF AN IRRADIATION DEVICE

PRIORITY STATEMENT

The present application hereby claims priority under 35 U.S.C. § 119 to German patent application number DE 10 2018 201 976.2 filed Feb. 8, 2018, the entire contents of which are hereby incorporated herein by reference.

FIELD

Embodiments of the invention generally relate to a filter device for a collimator of an irradiation device, comprising a plurality of filter disks arranged on a disk that is rotatable around an axis.

BACKGROUND

Irradiation devices are typically deployed in the form of X-ray devices comprising a radiation source and a radiation receiver. The radiation source emits the radiation, typically X-ray radiation. A collimator, which serves for shaping the beam path or the radiation cone, is connected immediately downstream of the radiation source in most cases. Owing to increased requirements it is aimed to reduce the installation size of such a collimator on irradiation devices of the aforethe type, such as mammography systems or other X-ray systems, for example. The purpose of reducing the size of the collimator is to improve accessibility to the patient. It is furthermore possible to extend the range of movement of the device in view of the fact that the smaller interference contour of the collimator allows a further degree of movement of the carrier arm of the system on which the radiation source and typically also the radiation receiver are arranged. A smaller, narrower collimator essentially enables the system to be kept slimmer in the region of the radiation source also.

A central element in the beam path is the filter device, with the aid of which different filters in the form of metallic filter plates composed of different filter materials having different filter strengths or filter properties can be positioned in the beam path. The installation size of the filter device is matched to the size of the collimator. It is positioned as close as possible in the direction of the focus on the top side of the collimator so that it can be implemented with the smallest possible footprint, and consequently in a space-saving manner.

A known filter device comprises a disk that is rotatable around an axis by way of a corresponding servo motor. Corresponding filter disks, typically three filter disks, are arranged on the disk. The desired filter disk is rotated into the beam path by rotation of the disk. Owing to the integration of the filter device into the collimator or, as the case may be, the collimator housing, the given installation space is utilized to the limit, not least with regard to the fact that a further aim is of course to implement the collimator itself in as compact a design as possible.

SUMMARY

The inventors have discovered that relocating the filter device closer toward the focus, which would lead to a reduction in size, is not possible because the filter device is already arranged on the top side of the collimator. Due to the rotation principle in known filter devices, the inventors have discovered that it is also not possible to reduce the size of the disk further on account of the filter disks arranged in fixed positions thereon. The inventors have discovered that a further obstacle to the size reduction is the fact that in more recent times there have been demands for an increase in the size of the beam path, for example in order to achieve a higher degree of flexibility in respect of the image acquisition techniques, which would lead to an additional increase in the size of the filter disks and consequently also inevitably to a necessary increase in the size of the disk carrying them.

At least one embodiment of the invention is therefore directed to disclosing a filter device that is improved by comparison with the known prior art and in particular enables the collimator to be reduced in size to a certain degree or the size of the beam path to be enlarged.

In at least one embodiment of the invention, a filter device includes a plurality of filter disks, each filter disk being mounted so as to be movable in the radial direction and tensioned by way of a respective spring element radially away from the axis or toward the axis against a guide contour effecting a radial movement of at least one filter disk.

In addition to the filter device embodiment of the invention, at least one embodiment of the invention further relates to a collimator comprising a filter device of at least one embodiment.

At least one embodiment of the invention furthermore relates to an irradiation device comprising a radiation source and a radiation receiver, as well as to a collimator comprising a filter device according to at least one embodiment of the invention.

To solve this problem, it is provided according to at least one embodiment of the invention, in a filter device, each filter disk is mounted so as to be movable in the radial direction and tensioned by way of a respective spring element radially away from the axis or toward the axis against a guide contour effecting a radial movement of at least one filter disk.

In the filter device according to at least one embodiment of the invention, the plurality of filter disks mounted on the disk that is rotatable by motorized device(s) around a central axis are no longer arranged in fixed positions, as generally known, but are instead movable radially relative to the axis. Each filter disk is tensioned separately by way of at least one spring element either radially away from the axis, i.e. is forced away from the axis by way of the compressed spring element, or is tensioned toward the axis, i.e. pulled actively toward the axis by way of the elongated spring element. The spring pretensioning is effected in each case against a positionally fixed guide contour, which is to say that each filter disk is tensioned against the positionally fixed guide contour or contour path. If the disk together with the filter disks is now rotated around the axis, the filter disks are pressed by way of the spring elements against the guide contour and slide along the latter due to the rotation.

The guide contour can now be configured in such a way that the filter disks, upon assuming corresponding rotational positions, are correspondingly moved radially relative to the axis. When a filter disk is moved or rotated into the beam path in the direction of its working position, this enables it to be displaced radially from its position close to the axis and to be introduced into the beam path. This therefore happens according to at least one embodiment of the invention by way of a combined translation and rotation movement, effected via the rotating disk and the spring element and guided via the guide contour of its contour path.

Having assumed the deployment position, the filter disk of at least one embodiment has undergone a maximum displacement and is located optimally positioned in the beam path. If the disk is rotated further, the filter disk is moved back again accordingly, once again by way of a combined translational and rotational action. The respective position may be detected via a sensor, via which the drive motor of the disk is controlled accordingly.

The filter device according to at least one embodiment of the invention consequently provides an active radial movement of the filter disks as a function of the rotational position. This enables a corresponding reduction in size of the filter device or the collimator at least in one direction. This is because, due to the fact that a defined radial movement of the filter disks relative to the axis is possible, i.e. the filter disks are therefore no longer fixed in position, corresponding degrees of freedom in respect of the disk movement are realized, which were not provided in the prior art, the positionally fixed arrangement of the filter disks in the prior art having required a correspondingly large construction in terms of the embodiment of the filter device.

A highly compact design of the filter device can be achieved in particular if at least the filter disks that are arranged adjacent to the axis, i.e. are therefore in the inoperative position or are not arranged in the beam path, overlap one another at least in sections. In other words, the filter disks are positioned slightly offset vertically, such that, depending on the rotational position of the disk, sections thereof can be slipped over one another, once again guided via the guide contour. In this way the filter disks can consequently be moved even closer to the axis, thus leading to a further reduction in size or narrowing of the filter device and as a result also of the collimator.

Alternatively to a reduction in size of the collimator, it is however possible, by way of at least one embodiment of the inventive concept, also to utilize larger filter disks since, starting from the installation space available in the prior art or with a configuration of the filter device in dimensions known in the prior art, correspondingly larger filter disks can be employed as a result of the radial movability of the filter disks, preferably in combination with the overlapping of the filter disks.

According to a first inventive embodiment variant of the filter device, it is provided that the guide contour guiding the filter disks tensioned away from the axis is realized as a path-shaped, rounded guide contour surrounding the filter disks. In this embodiment of the invention, the positionally fixed guide contour is consequently arranged externally around the internal filter disks. The guide contour is for example a plate having a sufficiently large-dimensioned recess with corresponding path-shaped rim or ribbon-shaped inner contour, the rim or inner contour forming the guiding contour path against which the filter disks are spring-loaded. The guide contour is a rounded guide contour which is correspondingly geometrically configured in accordance with the desired radial movement of the filter disks. It is preferably embodied as bulging convexly outward in at least one section such that the corresponding guide disk can be guided radially away from the axis in this region. Depending on the size of the filter disks and their desired arrangement (not overlapped, overlapped, etc.), a further convexity may also be provided, at the opposite end, for example. If three filter disks are provided, the guide contour is preferably embodied in an oval shape.

As described, such an external guide contour may be realized as a plate having a correspondingly geometrically configured recess in which the guide disks are accommodated. However, it is also conceivable to implement the guide contour as a positionally fixed, correspondingly geometrically shaped ring. All that is required on the part of the guide contour is that it is positionally fixed and sufficiently stable to allow the guide disks to be spring-loaded thereon and that the geometry of the guide contour, i.e. its contour path, enables a corresponding radial guidance.

As an alternative to the above-described invention embodiment alternative, it is conceivable that the guide contour guiding the filter disks tensioned toward the axis is implemented as a disk-shaped, rounded guide contour arranged inside the filter disks arranged around it. In this invention embodiment alternative, the guide disks are always tensioned inwardly toward the axis by way of the corresponding spring elements against the guide contour positioned inside the filter disk arrangement. In this case the positionally fixed guide contour is realized as a disk-shaped, rounded guide contour, i.e. as a guide disk arranged inside the filter disk arrangement having a corresponding path-shaped outer contour or path-shaped rim. The guide disks are tensioned continuously against it. During a rotation of the disk, and consequently also of the filter disks, the filter disks travel in contact with the guide contour around the latter and are displaced radially according to their geometry.

In this case, too, the guide contour is curved convexly outward in at least one section to allow the radial displacement. Here too, it can be embodied in an oval shape, in particular when three filter disks are provided, in particular when an overlap is possible.

The filter disks themselves are beneficially accommodated in a linear, radially directed guide arranged on the disk. For example, each filter disk has a corresponding, for example rectangular, frame in which a disk filter is accommodated. The rectangular frame can be accommodated in the corresponding radial linear guide and be guided thereon.

The spring elements are preferably embodied as compression springs, which can accordingly be readily dimensioned in order to generate the desired spring force or to allow the corresponding movement paths in the radial direction. As described, each filter disk can consist of a frame and a disk filter inserted therein, the frame being able to be guided along the guides in a simple manner. However, the respective spring element, for example the compression spring, can also be attached thereto in a correspondingly simple manner. It is also a simple matter to replace a disk filter, which merely has to be inserted into the frame.

In addition to the filter device embodiment of the invention, at least one embodiment of the invention further relates to a collimator comprising a filter device of at least one embodiment.

At least one embodiment of the invention furthermore relates to an irradiation device comprising a radiation source and a radiation receiver, as well as to a collimator comprising a filter device according to at least one embodiment of the invention.

BRIEF DESCRIPTION OF THE DRAWINGS

Further advantages and details of the invention will become apparent from the example embodiments described hereinbelow, as well as with reference to the drawings, in which.

DETAILED DESCRIPTION OF THE EXAMPLE EMBODIMENTS

Figure 1:
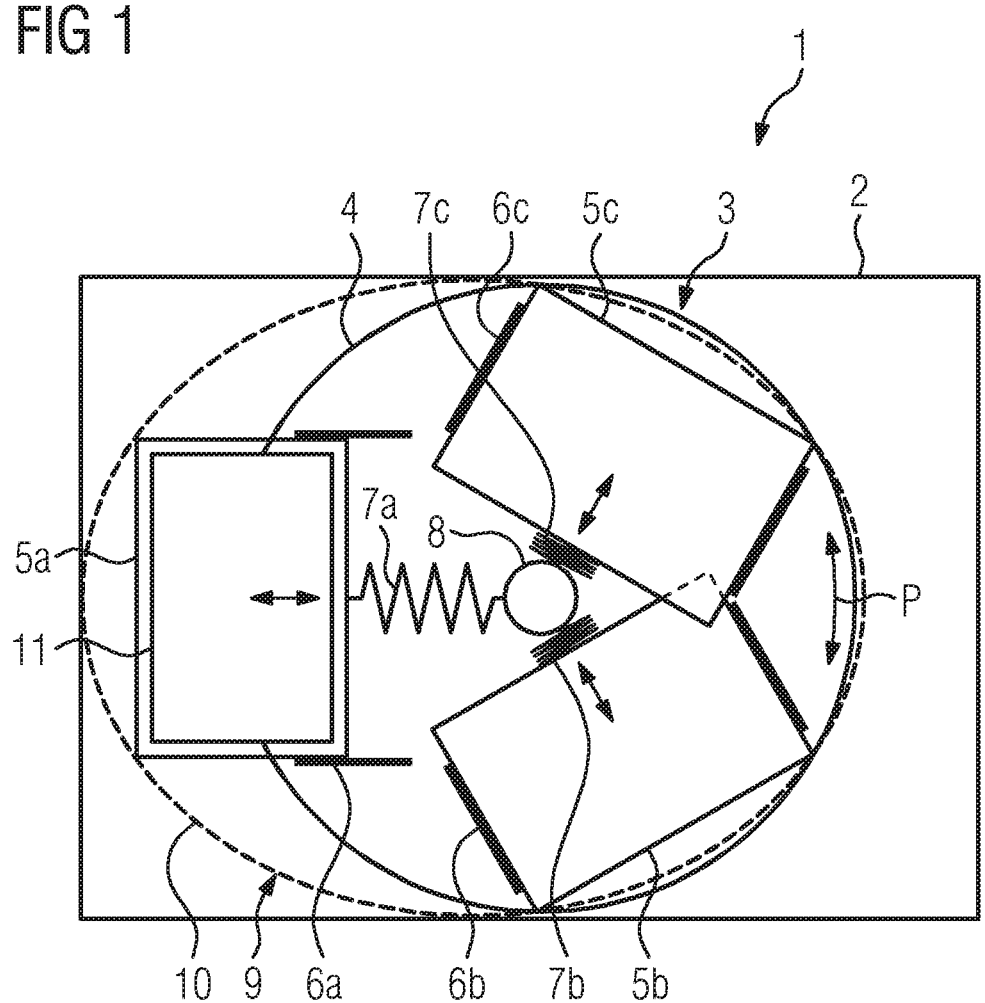
FIG. 1 shows a schematic diagram of an inventive filter device of a first embodiment variant in a first rotational position.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

Figure 5:
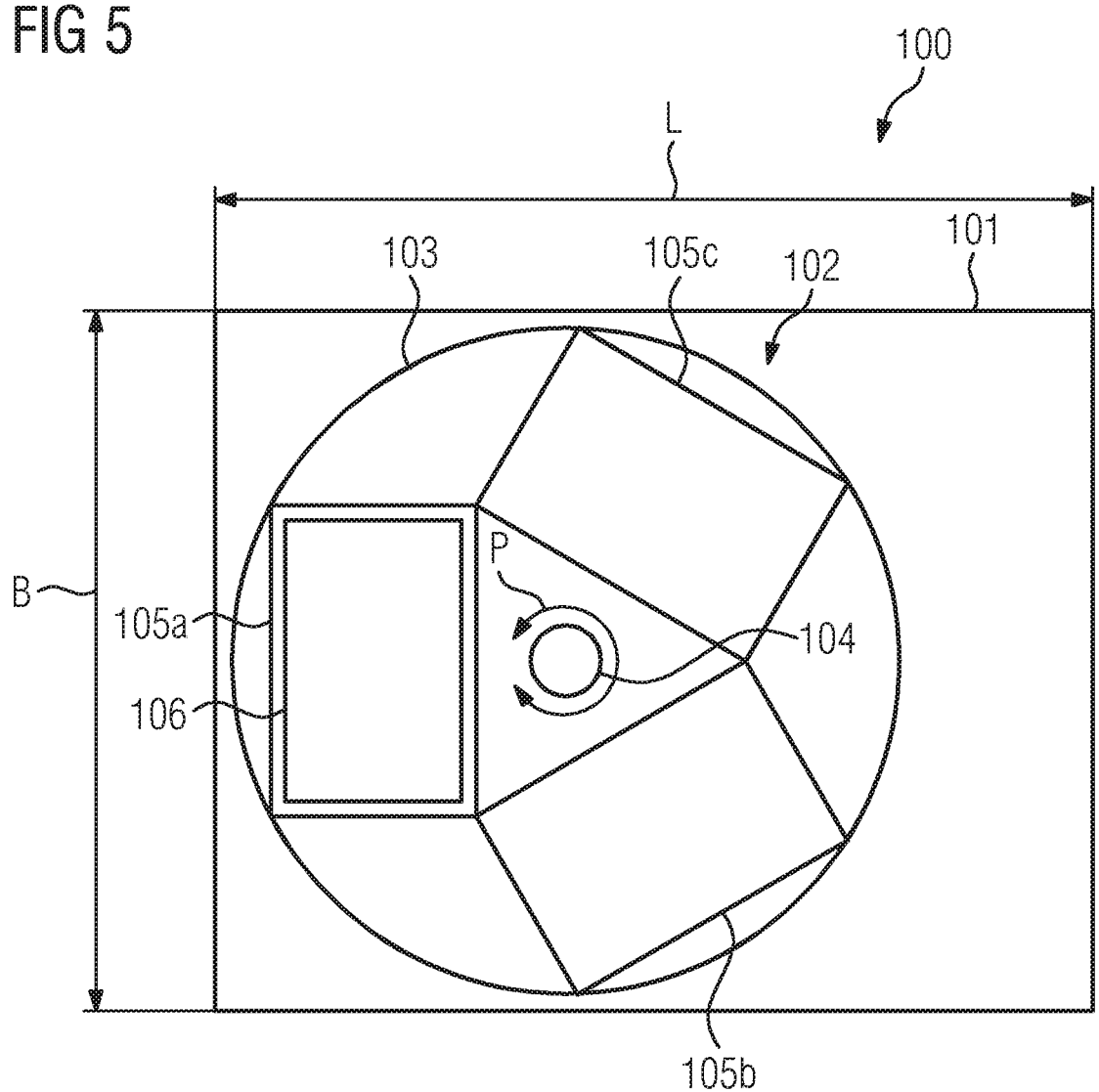
FIG. 5 shows a schematic diagram of a filter device according to the prior art.

Reference will firstly be made to FIG. 5, which shows a filter device according to the prior art.

FIG. 5 shows a schematic diagram of a collimator 100 having a housing 101 as well as a filter device 102 accommodated thereon or therein. The filter device 102 comprises a disk 103, which is rotatable around an axis 104, as represented by the double arrow P, by way of a drive motor (not shown in further detail) in conjunction with a corresponding position detection sensor or the like.

Three different filter disks 105*a*, 105*b* and 105*c*, which are positioned distributed around the axis 104, are arranged at fixed positions on the disk 103.

In the arrangement shown, the filter disk 105*a* is located in the "working position" immediately adjacent to a radiation exit window 106 of a radiation source (not shown in further detail). By rotating the disk 103 it is possible to turn each filter disk 105*a*, 105*b* and 105*c* adjacent to the radiation exit window 106, i.e. consequently to move it into the beam path.

The housing 101 has a length L and a width B. As can be seen, the size of the filter device 102 or disk 103 is dimensioned according to the size of the housing 101, in particular with regard to its width. Owing to the embodiment of the filter device 102, a further reduction in size is not possible.

FIG. 1 shows an embodiment of an inventive collimator 1 having an embodiment of an inventive filter device 3 arranged on or in its housing 2. The filter device 3 comprises a disk 4 that is rotatable by way of a drive motor and is detectable in respect of its position e.g. via a sensor, three filter disks 5*a*, 5*b*, 5*c* being arranged on the disk 4 in the example shown. In most cases the filter disks are corresponding metallic filter plates having different filter properties.

Each filter disk 5*a*, 5*b*, 5*c* comprises for example a frame (not shown in further detail) and a disk filter inserted therein, i.e. the actual filter plate.

In the example shown, three guides 6*a*, 6*b*, 6*c* are provided on the disk 4, enabling a radial linear guiding of the filter disks 5*a*, 5*b*, 5*c* that are movably arranged on the disk 4, as represented by the double arrows. If, as described, each of the filter disks 5*a*, 5*b*, 5*c* has a frame, the frame can be guided by way of its sides along the corresponding guides 6*a*, 6*b*, 6*c*.

To allow the radial movement of the filter disks 5*a*, 5*b*, 5*c*, each is connected to a spring element 7*a*, 7*b*, 7*c*, which is embodied for example as a compression spring and is attached at one end close to the axis 8 on the disk side and at the other end to the respective filter disk 5*a*, 5*b*, 5*c*, for example to its frame. In this inventive embodiment, the configuration is such that each spring element 7*a*, 7*b*, 7*c* presses the respective filter disk 5*a*, 5*b*, 5*c* radially outward, i.e. away from the axis 8. Each filter disk 5*a*, 5*b*, 5*c* is pressed against a common, positionally fixed guide contour 9 surrounding it on the outside. The guide contour 9 is for example a plate (not shown in further detail) having a corresponding recess or a circumferential ridge or ring, the inner border of which forms a guide path 10 against which each filter disk 5a, 5b, 5c is spring-loaded.

As FIG. 1 shows, the guide contour 9 has a substantially rounded, yet oval geometry, i.e. the guide path 10 is rounded or oval. As the filter disks 5a, 5b, 5c are spring-loaded against the guide path 10, they are consequently displaced radially by way of the spring element in conjunction with the guide contour according to the rotational position of the disk and hence the rotational position of the respective filter disk 5a, 5b, 5c. Depending on the rotational position, this results in a movement away from the axis 8 or toward the axis 8.

In the illustrated example embodiment, the filter disk 5a is located in the "working position" adjacent to the radiation exit window 11. If a change of disk is now to take place and the filter disk 5c is to be rotated into the beam path, the disk 4 is rotated by way of the motor (not shown in further detail). This necessarily causes a rotation of the filter disks 5a, 5b, 5c also, which travel along the guide path 10. Since the latter changes its distance relative to the axis 8 around the circumference, the consequence is that each filter disk 5a, 5b, 5c likewise changes its distance relative to the axis 8 depending on the rotational position of the disk 4.

Figure 2:
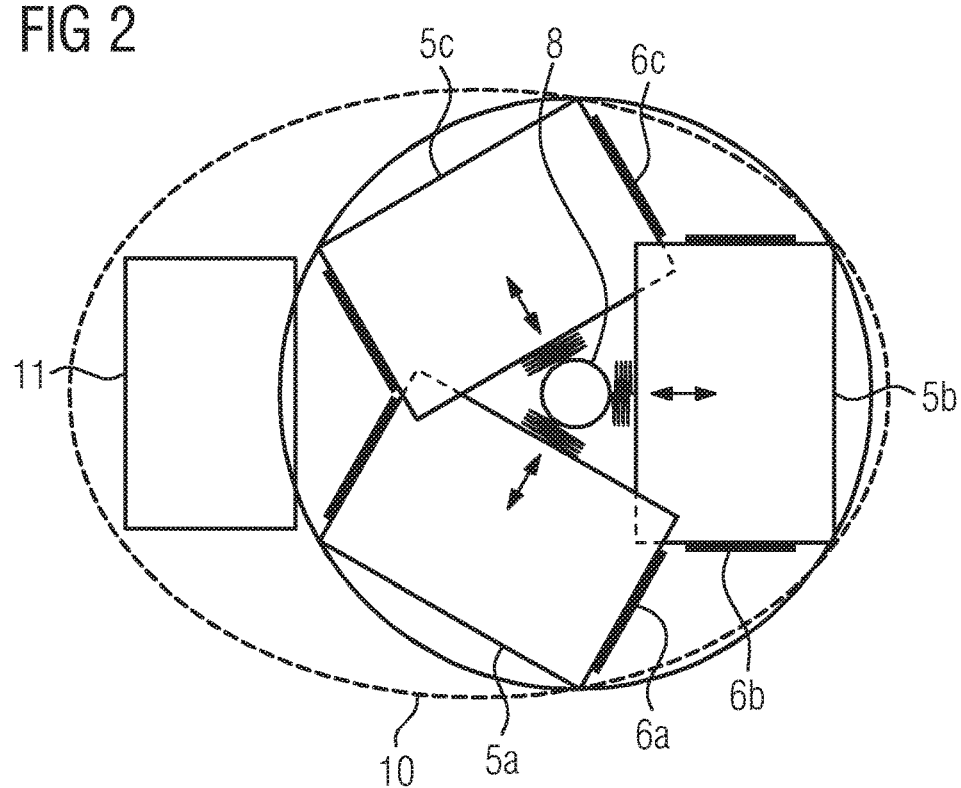
FIG. 2 shows the filter device from FIG. 1 in a second rotational position.

FIG. 2 shows a view in which the disk 4 has been rotated counterclockwise by a corresponding angle of rotation. As can be seen, the filter disk 5a has been rotated out of its working position and, due to being guided along the guide path 10, it is shifted relative to the axis 8 along the guide 6a on account of the change in position.

The filter disk 5b, for its part, has been guided outwardly to some extent because—in a similar manner to the left-hand side—the guide path 10 has a convexity toward the right-hand side. It has therefore been shifted somewhat radially outwardly along the guide 6b.

Similarly, the filter disk 5c has also been pressed slightly radially outwardly along its guide 6c by way of the corresponding spring element.

Figure 3:
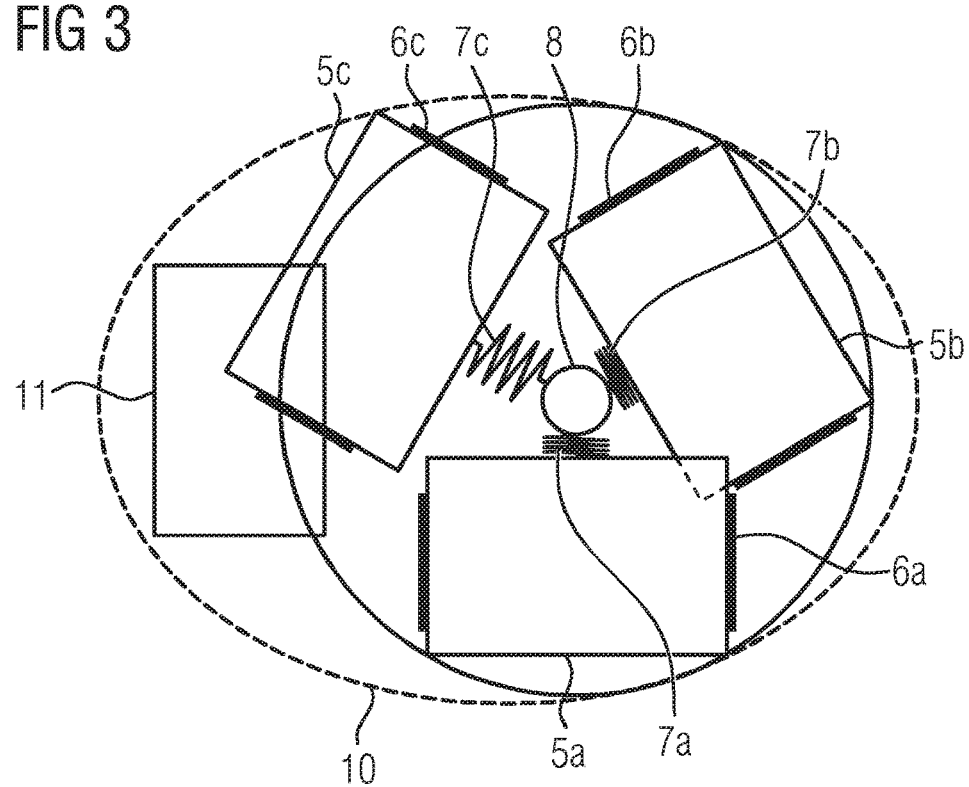
FIG. 3 shows the filter device from FIG. 1 in a third rotational position.

In a further rotation, see FIG. 3, the filter disk 5a is shifted even further in the direction of the central axis 8 with compression of its spring element 7a. The filter disk 5b is likewise shifted somewhat back again in the direction of the axis 8 with compression of the spring element 7b. The filter disk 5c, on the other hand, since it is rotated into the region of the left-hand convexity of the guide path 10, is pressed further outward, i.e. its spring element 7c relaxes further. The filter disk 5c is located already partially overlapping with the radiation exit window 11, though it is not yet in the working position. The latter is assumed when filter disk is rotated further, such that a position corresponding to FIG. 1 then results.

As shown, see FIGS. 1-3, the filter disks partially overlap when they are in the "non-working position" inserted adjacent to the axis 8. For this purpose, the filter disks 5a, 5b, 5c are slightly offset vertically, i.e. arranged spaced apart from one another in the axial direction, in other words are located slightly in different planes, such that, once again guided by way of the guide path 10 of the guide contour 9, they can be slipped over one another in sections with their respective corner regions. This results in a narrowing of the filter device 3, which is to say that the diameter of the disk 4 can be reduced, with the result that the width B of the collimator 1 can be reduced.

On the other hand, if no reduction in the size of the collimator, but rather an enlargement of the radiation cone, and consequently an increase in the size of the filter disks, is desired, this can also be achieved. This is because the radial movability, in particular in conjunction with the possibility of overlapping, permits larger filter disks to be used than in the prior art.

In the inventive embodiment according to FIGS. 1-3, the guide contour 9 surrounds the filter disks 5a, 5b, 5c externally, i.e. the filter disks are located inside the guide contour 9. The spring elements 7a, 7b, 7c consequently press the filter disks 5a, 5b, 5c radially outward against the guide contour 9.

Figure 4:
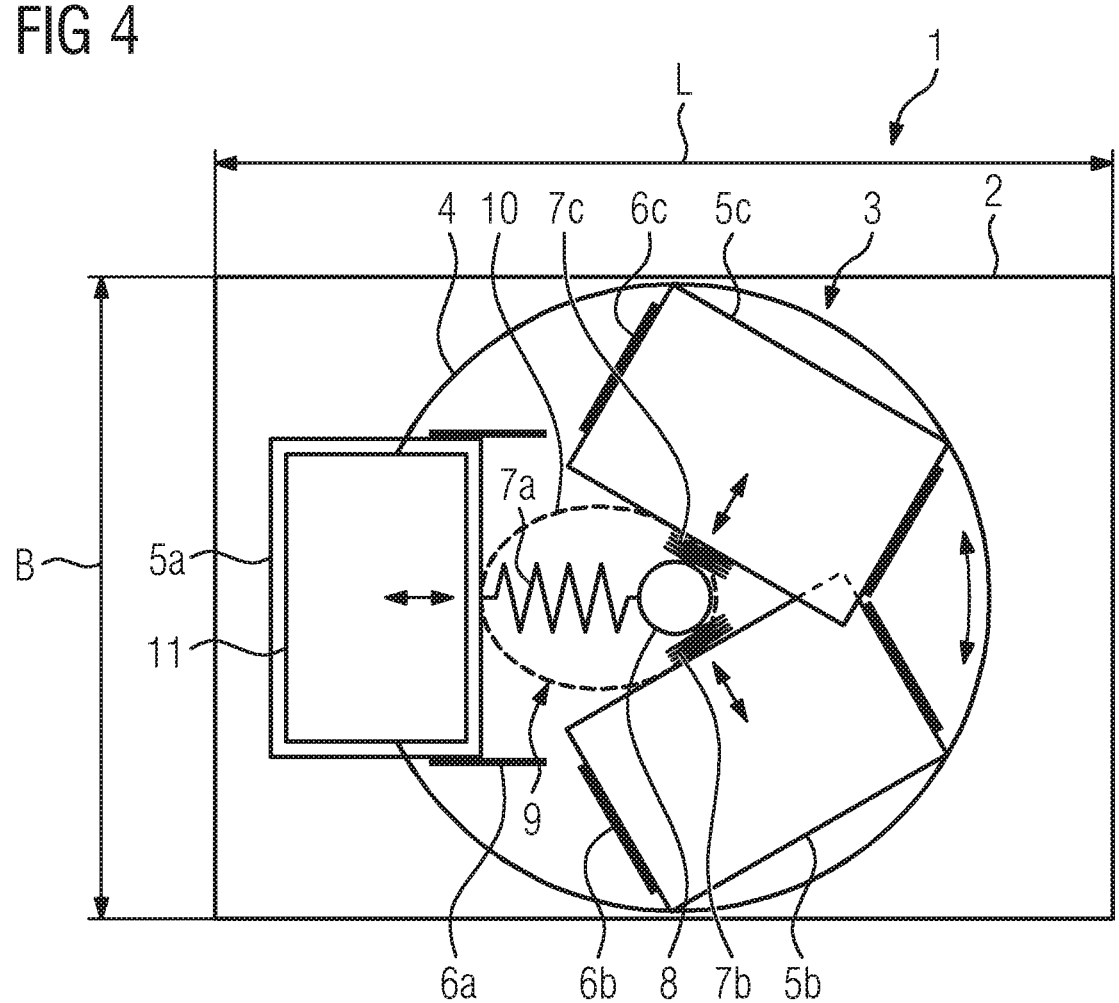
FIG. 4 shows an inventive filter device in a second embodiment variant.

FIG. 4 shows an embodiment of an inventive filter device 3 operating in an inverse manner thereto, like reference signs being used for like components. The filter device 3 is likewise accommodated in a housing 2 of a collimator 1. In turn, it comprises a disk 4 that is rotatable via a motor and three filter disks 5a, 5b, 5c arranged thereon, which are arranged so as to be linearly movable along corresponding linearly acting guides 6a, 6b, 6c, as indicated by the double arrows.

A spring element 7a, 7b, 7c is again assigned to each filter disk 5a, 5b, 5c. In this case, however, the spring elements 7a, 7b, 7c permanently pull the filter disks 5a, 5b, 5c toward the axis 8, i.e. they are pretensioned in the direction of the axis 8. In this case, too, a positionally fixed guide contour 9 is provided having a guide path 10 embodied on its outer circumference, against which guide path 10 the filter disks 5a, 5b, 5c are tensioned.

As can be seen, the guide contour 9 or the guide path 10 is rounded or oval-shaped in this case also, such that, during a disk rotation, the filter disks 5a, 5b, 5c sliding along the disk on account of being tensioned against it are actively pressed outward depending on their rotational position and as a result the respective spring element is tensioned or, as the case may be, they are pulled inward again by way of the respective spring element according to their rotational position. Consequently, during a rotation of the disk 4, a corresponding radial movement of the filter disks 5a, 5b, 5c that is effected due to the geometry by way of the guide contour 9 in conjunction with the spring elements 7a, 7b, 7c can be achieved in this case too. Here, too, the filter disks 5a, 5b, 5c overlap depending on their position or rotational position, thereby enabling a corresponding reduction in size of the structure of the filter device 3 to be achieved, or alternatively allowing larger filter disks to be used.

The number of three filter disks 5a, 5b, 5c, as well as the geometric embodiment of the respective guide contours, is purely by way of example. It is self-evident that fewer or more filter disks may also be used, as then, depending on number, other geometries can accordingly be chosen on the part of the guide contour 9.

Although the invention has been illustrated and described in more detail on the basis of the preferred example embodiment, the invention is not limited by the disclosed examples and other variations may be derived herefrom by the person skilled in the art without leaving the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A filter device for a collimator of an irradiation device, comprising:
    a plurality of filter disks, arranged on a disk rotatable around an axis, each respective filter disk, of the plurality of filter disks, being mounted so as to be movable in a radial direction and being tensioned via a respective spring element radially away from the axis or toward the axis against a guide contour, to effect a radial movement of at least one filter disk of the plurality of filter disks.

2. The filter device as claimed in claim 1, wherein at least the filter disks, arranged adjacent to the axis, overlap in sections.

3. The filter device of claim 1, wherein the guide contour, to guide the plurality of filter disks tensioned away from the axis, is embodied as a path-shaped, rounded guide contour surrounding the plurality of filter disks.

4. The filter device of claim 3, wherein the guide contour is curved convexly outward in at least one section.

5. The filter device of claim 4, wherein the plurality of filter disks include three filter disks, and wherein the guide contour is embodied in an oval shape.

6. The filter device of claim 1, wherein the guide contour, to guide the plurality of filter disks tensioned toward the axis, is embodied as a disk-shaped, rounded guide contour arranged inside the filter disks arranged around the guide contour.

7. The filter device of claim 6, wherein the guide contour is curved convexly outward in at least one section.

8. The filter device of claim 7, wherein the plurality of filter disks include three filter disks, and wherein the guide contour is embodied in an oval shape.

9. The filter device of claim 1, wherein each filter disk, of the plurality of filter disks, is accommodated in a linear, radially directed guide arranged on the disk.

10. The filter device of claim 1, wherein compression springs are provided as spring elements.

11. The filter device of claim 1, wherein each filter disk, of the plurality of filter disks, consists of a frame and a disk filter inserted into the frame.

12. A collimator, comprising:
    the filter device of claim 1.

13. An irradiation device, comprising:
    a radiation source;
    a radiation receiver; and
    the collimator of claim 12.

14. The filter device of claim 1, wherein the guide contour, to guide the plurality of filter disks tensioned away from the axis, is embodied as a path-shaped, rounded guide contour surrounding the plurality of filter disks.

15. The filter device of claim 14, wherein the guide contour is curved convexly outward in at least one section.

16. The filter device of claim 15, wherein the plurality of filter disks include three filter disks, and wherein the guide contour is embodied in an oval shape.

17. The filter device of claim 2, wherein the guide contour, to guide the plurality of filter disks tensioned toward the axis, is embodied as a disk-shaped, rounded guide contour arranged inside the filter disks arranged around the guide contour.

18. The filter device of claim 17, wherein the guide contour is curved convexly outward in at least one section.

19. The filter device of claim 18, wherein the plurality of filter disks include three filter disks, and wherein the guide contour is embodied in an oval shape.

20. A collimator, comprising:
    the filter device of claim 2.

* * * * *